(12) United States Patent
Aufreiter et al.

(10) Patent No.: US 12,607,550 B2
(45) Date of Patent: Apr. 21, 2026

(54) SENSOR DEVICE AND METHOD FOR CHARACTERIZING METAL CHIPS

(71) Applicant: INMOX GMBH, Vienna (AT)

(72) Inventors: Michael Aufreiter, Freistadt (AT);
Daniel Kagerbauer, Vienna (AT)

(73) Assignee: INMOX GMBH, Vienna (AT)

( * ) Notice: Subject to any disclaimer, the term of this patent is extended or adjusted under 35 U.S.C. 154(b) by 57 days.

(21) Appl. No.: 18/575,709

(22) PCT Filed: Jul. 1, 2022

(86) PCT No.: PCT/EP2022/068308
§ 371 (c)(1),
(2) Date: Dec. 29, 2023

(87) PCT Pub. No.: WO2023/275372
PCT Pub. Date: Jan. 5, 2023

(65) Prior Publication Data
US 2024/0310267 A1     Sep. 19, 2024

(30) Foreign Application Priority Data
Jul. 2, 2021    (DE) ..................... 10 2021 117 119.9

(51) Int. Cl.
*G01N 15/1031*     (2024.01)
*G01N 15/00*     (2024.01)
(Continued)

(52) U.S. Cl.
CPC ..... *G01N 15/1031* (2013.01); *G01N 33/2858* (2013.01); *G01N 2015/0053* (2013.01); *G01N 2015/1029* (2024.01)

(58) Field of Classification Search
CPC .......... G01N 15/1031; G01N 15/0266; G01N 33/2858; G01N 2015/0053; G01N 2015/1029; G01N 27/80; G01M 13/021
(Continued)

(56) References Cited

U.S. PATENT DOCUMENTS 5,214,377 A * 5/1993 Maurice ................... G01V 3/08
                                                                250/225
5,357,197 A * 10/1994 Sorkin ............... G01N 33/2858
                                                                324/226
(Continued)

FOREIGN PATENT DOCUMENTS

DE     102010011936 A1     9/2011
EP         2121203 B1     12/2010
(Continued)

OTHER PUBLICATIONS

International Search Report for Application No. PCT/EP2022/068308 dated Dec. 5, 2022 (53 pages including English translation).
(Continued)

*Primary Examiner* — Christopher P McAndrew
(74) *Attorney, Agent, or Firm* — Michael Best & Friedrich LLP

(57)     ABSTRACT

The present invention relates to a sensor device for characterizing a chip, comprising a chip analysis area, wherein the chip analysis area is a spatial region; a signal generator having at least one transmitting coil, wherein the signal generator is configured to generate an electrical exciter signal and to couple said signal into the chip analysis area as a magnetic signal by means of the transmitting coil; a chip classifier having at least one receiving coil, wherein the chip classifier is configured to receive a chip signal from the chip analysis area by means of the receiving coil, wherein the chip signal is a magnetization signal excited by the exciter signal and generated by at least one chip to be classified. The
(Continued)

100 present invention further relates to a method for characterizing a chip by means of a sensor device comprising at least one signal generator and one chip classifier.

20 Claims, 4 Drawing Sheets

(51) Int. Cl.
 *G01N 15/10* (2024.01)
 *G01N 33/28* (2006.01)
(58) Field of Classification Search
 USPC ......................................................... 324/654
 See application file for complete search history.

(56) References Cited

U.S. PATENT DOCUMENTS

| | | | | |
|---|---|---|---|---|
| 5,444,367 A | * | 8/1995 | Kempster .......... | G01N 15/0656 |
| | | | | 324/225 |
| 5,742,234 A | * | 4/1998 | Owen ................ | G01N 15/1031 |
| | | | | 340/627 |
| 2016/0334351 A1 | * | 11/2016 | Lu .......................... | G01N 27/06 |
| 2017/0122859 A1 | * | 5/2017 | Nishigaki .......... | G01N 15/1023 |
| 2017/0269036 A1 | * | 9/2017 | Foord .................. | G01N 27/023 |
| 2018/0011042 A1 | * | 1/2018 | Sells ...................... | G01N 27/06 |
| 2018/0185854 A1 | * | 7/2018 | Liu ........................ | C12M 1/266 |
| 2019/0201084 A1 | * | 7/2019 | Shelton, IV .......... | A61B 34/37 |
| 2019/0201085 A1 | * | 7/2019 | Shelton, IV ....... | A61B 18/1206 |

FOREIGN PATENT DOCUMENTS

| | | | | |
|---|---|---|---|---|
| EP | 2455774 A1 | 5/2012 | | |
| EP | 2533073 A2 | 12/2012 | | |
| EP | 1933129 B1 | 2/2013 | | |
| EP | 3349000 A1 | 7/2018 | | |
| EP | 3581916 A1 | 12/2019 | | |
| JP | 2008039394 A | 2/2008 | | |
| WO | 2015140411 A2 | 9/2015 | | |
| WO | WO-2018134609 A1 | * | 7/2018 | ....... G01N 33/54326 |

OTHER PUBLICATIONS

German Patent Office Examination Report for Application No. 102021117119.9 dated Mar. 1, 2023 (14 pages including English translation).
Japanese Patent Office Action for Application No. 2023580983 dated Dec. 12, 2025 (28 pages including English machine translation).

* cited by examiner

SENSOR DEVICE AND METHOD FOR CHARACTERIZING METAL CHIPS

The present invention relates to a sensor device for characterizing a chip. The present invention further relates to a method for characterizing a chip by means of a sensor device.

Transmissions are fundamentally known. Transmissions serve for transmitting and transforming motions, energy, and/or forces and are used for this purpose in various technical systems, such as in wind power plants, on ships, in helicopters, in cable cars, or in vehicles.

It is thereby known that transmissions undergo wear in practical use because they are mechanically loaded when transmitting and transforming motions, energy, and/or forces. To reduce wear, functionally critical components such as gears or rolling bearings are lubricated, with the objective of achieving a hydrodynamic lubrication state in order to reduce the mechanical wear in the transmission and to protect the transmission from overheating.

A hydrodynamic lubrication state cannot always be guaranteed during operation, for example due to dynamic loads and due to starting and braking processes, so that components in the transmission undergo wear. Thus various damage occurs to gears and to rolling or plain bearings, such as pitting damage, micropitting, or galling. The damage or failure modes are thereby subject to various standards (e.g., DIN 3979). As defined in said standards, wear is understood to be the ablation of material due to the rubbing of two bodies against each other. This damage is referred to below as wear.

The wear or the detached transmission material thus enters the lubrication circuit and is present in the lubrication circuit as artifacts in the form of metal particles or metal chips. In addition, other suspended matter or different phases may also be present in the lubrication circuit, such as nonmetal particles including soot or air bubbles.

Because maintenance and repair of transmission is sometimes associated with great effort, such maintenance work or repairs may lead to long periods of downtime causing high costs from time to time. In addition, for some technical systems, a high level of operational reliability is desired, for example in helicopters, where wear is to be monitored to a particularly high degree.

For this reason, efforts are made to monitor transmissions.

One known type of monitoring of transmissions is known as particle counters for counting the number of metal wear particles of transmission components. Said particle counters thereby use either optical or electrical methods. When the electrical method is used, an electrical field is induced in a lubrication line, for example, in order to count metal chips.

A problem with such systems, however, is that such systems fundamentally allow only a quantitative conclusion about wear, but no conclusion about the type of wear or any transmission damage. The number of particles counted in the lubrication circuit is thus only a quantitative indicator in order to be able to draw a conclusion of transmission damage.

In addition, said systems are dependent on wear particles moving (circulatory lubrication) so that said particles are detected by the particle counter.

For optical systems, it is problematic that said systems can function or distinguish between metal particles, air bubbles, or soot only to a limited degree in dark oils, because said systems cannot detect the particles in the dark oil.

In order to increase the safety, predictability, and cost effectiveness of a technical system having a transmission, it would therefore be desirable not only to verify the wear quantitatively by means of counting particles, but also to be able to qualitatively evaluate the wear and to differentiate the wear into critical and uncritical wear indications. This is currently possible only by means of laboratory testing or by on-site "estimations" by an expert.

The German Patent and Trademark Office researched the following prior art:

EP 1 933 129 B1, EP 2 121 203 B1, EP 3 349 000 A1, DE 10 2010 011 936 A1, WO 2015/140 411 A2, EP 2 455 774 A1. The publications EP 1 933 129 B1, EP 3 349 000 A1 each relate to devices and methods, wherein a change in impedance between a measurement coil and a reference coil caused by a metal particle is compared for characterizing metal particles. The publication EP 2 121 203 B1 identifies metal objects on a conveyor belt in that a magnetically uninfluenced state of a coil is compared with a magnetically influenced state. The publications DE 10 2010 011 936 A1 and WO 2015 140 411 A2 relate to measuring arrangements for analyzing samples in a sample container. The publication EP 2 455 774 A1 relates to a sensor device having a chip collector having a permanent magnet. When the attractive effect of the permanent magnet is to be nullified, an opposing field is generated by means of an induction coil and the magnetically held chip can be removed.

The object of the present invention is therefore to address one of the problems indicated above, to improve the general state of the art, or to provide an alternative to the prior art. In particular, a solution is to be provided by means of which, in addition to detecting a chip, a continuous monitoring and evaluating of the chip is made possible in order to be able to evaluated a hazard potential of wear on site and during operation.

According to the invention, a sensor device according to claim 1 is thus proposed and a sensor device for characterizing a chip is provided. Characterizing thereby means that properties of the chip are identified or determined by means of the sensor device, such as a hardness of the chip; a chip size, that is, the volume thereof; or a material of which the chip is made. The hardness may also synonymously be construed as a hardness class. The characterization may also be construed as analysis of the chip. It is thus proposed that a chip is characterized and evaluated by means of the sensor device on site and during operation. The chip is a particle having separated from a transmission component, for example. The chip can thus be understood as a metal particle or metal contaminant. The chip can also be referred to synonymously as a flake.

The chip is preferably a metal chip or a metallic chip.

The sensor device comprises a chip analysis area, wherein the chip analysis area is a spatial region. The chip analysis area describes a spatial region within which the characterization and analysis of the chip is performed. The chip may be held in the analysis area for this purpose by a chip collector, for example, in order to provide a stationary analysis of the chip in the analysis area. The chip analysis area is a spatial segment within a lubrication line in a lubricating oil circuit of a transmission, for example, or a spatial segment in a coolant line in a coolant circuit.

Furthermore, the sensor device comprises a signal generator having at least one transmitting coil, wherein the signal generator is configured to generate an electrical exciter signal and to couple said signal into the chip analysis area by means of the transmitting coil.

It is thus proposed to generate an electrical signal by means of a signal generator, for example having as a signal source a function generator electrically conductively connected to the transmitting coil. The electrical exciter signal may be an alternating signal, for example a sinusoidal signal. The transmitting coil is, for example, a copper coil wound about a magnetic core. The transmitting coil may be construed as synonymous with an exciter coil. The coupling may also be construed as inducing. It is thus proposed to introduce an electromagnetic signal into the chip analysis area in which a chip or a plurality of chips is or are disposed. The chip or optionally the chips are thus excited by the exciter signal coupled into the chip analysis area as a magnetic signal. The signal generator having the transmitting coil may thus also be construed as a transmitting unit for introducing an electrical signal or a magnetic signal into the chip analysis area for electrically or magnetically exciting the chip.

The sensor device further comprises a chip classifier having at least one receiving sensor, wherein the chip classifier is configured to receive a chip signal from the chip analysis area by means of the receiving sensor, wherein the chip signal is a magnetization signal excited by the exciter signal and generated by at least one chip to be classified. The receiving sensor is, for example, a receiving coil, a receiving element configured to utilize the Hall effect for receiving the chip signal (Hall-effect sensor), a receiving element configured to utilize the magnetoresistive effect for receiving the chip signal (magnetoresistive sensor), or the like. It is thus proposed to measure the chip signal by means of the receiving sensor.

The sensor device preferably comprises a chip classifier having at least one receiving sensor, wherein the chip classifier is configured to receive a chip signal from the chip analysis area by means of the receiving coil, wherein the chip signal is a magnetization signal excited by the exciter signal and generated by at least one chip to be classified.

It is thus proposed to receive a magnetic signal exiting the chip analysis area, namely the chip signal, by means of the chip classifier. The chip signal is a magnetic signal generated by the chip due to the exciting thereof by the exciter signal. As described above, an electromagnetic signal is introduced into the chip analysis area for electrically or magnetically exciting the chip by means of the signal generator and the transmitting coil. Due to said magnetic excitation, the chip generates a measurable signal measured at a phase shift to the exciter signal, preferably by means of a receiving coil. The chip signal induces a voltage in the receiving coil, for example, and generates a measurable voltage or a measurable current. The chip classifier may thus also be construed as a receiving or measuring unit for measuring the chip signal, preferably by means of a receiving coil. The receiving coil may thereby be implemented as a plurality of coils interconnected in an array. The receiving coil or coils and/or the transmitting coil is or are wound copper coils, for example.

This fundamental principle applies analogously to at least one receiving sensor implemented having a receiving element configured to utilize a Hall effect and/or a magnetoresistive effect for receiving the chip signal. Due to the magnetic excitation, the chip generates a measurable signal measured by means of the receiving element at a phase shift from the exciter signal, namely the chip signal. The chip signal induces a voltage in the receiving element and generates a measurable voltage or a measurable current, or leads to a measurable change in resistance in the receiving element. The chip classifier may thus also be construed as a receiving or measuring unit for measuring the chip signal by means of a Hall-effect sensor and/or a magnetoresistive sensor. A receiving element configured to utilize a Hall effect and/or a magnetoresistive effect for receiving the chip signal may also be referred to as a Hall-effect sensor and/or a magnetoresistive sensor.

The receiving element may thereby be implemented as a plurality of sensors interconnected in an array.

A plurality of an item or an object is present when at least two items or objects are present.

The chip classifier is further configured to classify the at least one chip in the chip analysis area by evaluating a phase shift between the exciter signal and the chip signal and/or an amplitude of the chip signal.

It is thus proposed that the chip classifier also functions as an evaluation unit or comprises such a unit. The chip classifier thus considers the exciter signal and the chip signal and can determine and/or process a phase shift between the two signals. In addition or alternatively, the chip classifier can determine and/or process an amplitude of the chip signal. The phase shift is also known as the phase difference or phasing and describes two sinusoidal vibrations, for example, having phase angles shifted relative to each other, when the period lengths do match but the zero intercept points are different. The amplitude of the chip signal describes the maximum deflection of the chip signal from the position of the arithmetic mean. The amplitude is also known as the peak value.

Classifying thus refers to the fact that the properties of the chip to be classified, such as a hardness or hardness class of the chip, a chip size, or a chip material are to be determined. It is understood that classifying also comprises detecting the chip. The sensor device is accordingly further configured to detect the at least one chip in the chip analysis area by evaluating a phase shift between the exciter signal and the chip signal and/or an amplitude of the chip signal.

It is preferably proposed that an absolute value of the amplitude of the chip signal is evaluated or considered for characterizing the chip. It is thus proposed to determine the amplitude as an absolute value.

It has been realized that metal chips having different properties can be present and the different properties allow conclusions to be drawn about the extent and/or origin of the damage or wear. In particular, it has also been realized that the hardness of the chip is a suitable indicator for whether critical or less critical transmission damage or transmission wear is present.

By evaluating the phase shift and/or the amplitude, a conclusion about a hardness of the chip can be drawn. When a magnetically hard chip is detected, for example, then it can be assumed that a critical transmission component has been damaged. Critical transmission components are typically hardened and have magnetically hard properties for this reason. If, in contrast, a magnetically soft chip is detected, then uncritical wear can be assumed, because magnetically soft metals are used for less relevant transmission components.

By evaluating the phase shift and/or the amplitude, a conclusion about a chip size, in addition to the hardness, can also be drawn. The chip size can also be construed as the chip volume. When a large chip is detected, a conclusion about an extent of the damage of a transmission component can be drawn.

In addition, by evaluating the phase shift and/or the amplitude, it is also possible to determine a material of the chip, because the chips made of different materials have different magnetic properties, such as different susceptibility.

It is thus proposed to use chips as a wear indicator in the lubrication circuit of a transmission. The characterization of the chips, synonymously also construed as classification, thereby takes place by evaluating the phase shift between the exciter signal and the chip signal and/or the amplitude of the chip signal.

An intelligent sensor for monitoring the condition of a transmission is thus provided and can be used in various technical systems.

It should be understood that the evaluation of a phase shift between the exciter signal and the chip signal and/or an amplitude of the chip signal is optional in embodiments in order to classify the at least one chip in the chip analysis area. Other or further evaluation methods may be provided in order to classify the at least one chip in the chip analysis area.

The chip classifier is preferably configured to classify the at least one chip in the chip analysis area as a function of the chip signal and/or of the exciter signal by means of an evaluation method, namely by means of at least one evaluation method from the list of evaluation methods comprising:

classification by means of a frequency analysis, for example by means of a Fourier transform, such as a DFT (discrete Fourier transform), an FFT (fast Fourier transform), or an STFT (short-term Fourier transform);

classification by means of a wavelet analysis;

classification by means of an artificial neural network.

The chip classifier is preferably configured at least to determine a hardness, a chip size, and/or a chip material of the at least one chip to be classified. Said parameters are determined in that magnetic parameters, such as an area under a hysteresis curve, a magnetization, or other magnetic properties are derived or determined by analyzing the phase shift and/or the amplitude of the chip signal, and/or are derived or determined by evaluating by means of an evaluation method.

The receiving sensor is preferably implemented having a receiving coil. A chip classifier having at least one receiving coil is thus proposed, wherein the chip classifier is configured to receive a chip signal from the chip analysis area by means of the receiving coil, wherein the chip signal is a magnetization signal excited by the exciter signal and generated by at least one chip to be classified. The principle of operation using a receiving coil has already been described above. The chip signal induces a voltage in the receiving coil and generates a measurable voltage or a measurable current. The chip classifier may thus also be construed as a receiving or measuring unit for measuring the chip signal by means of a receiving coil.

The receiving sensor is preferably implemented having a receiving element configured to utilize a Hall effect and/or a magnetoresistive effect for receiving the chip signal. The chip classifier is thus configured to receive a chip signal from the chip analysis area by means of a Hall-effect sensor and/or by means of a magnetoresistive sensor. It is thus proposed, in addition or alternatively to the receiving coil, to use a Hall-effect sensor and/or a magnetoresistive sensor as the receiver for the chip signal. The Hall effect and magnetoresistive effect are fundamentally known. It is thus proposed to use sensors for measuring magnetic fields or magnetic signals utilizing the Hall effect and/or the magnetoresistive effect. The chip signal from the chip analysis area is thus measured by means of the Hall-effect sensor and/or the magnetoresistive sensor, wherein the chip signal is a magnetization signal excited by the exciter signal and generated by at least one chip to be classified. A combination of a receiving coil, Hall-effect sensor, and/or magnetoresistive sensor may also be provided.

It is preferably proposed that the chip classifier evaluates an in-phase component for identifying a chip size of the chip and/or a chip material of the chip, said component further being proportional to a magnetization of the chip. The so-called in-phase component is thereby known from signal processing and is determined in that a demodulation of the exciter signal and of the chip signal is performed for the original phasing (in phase). It has been realized here that the in-phase component is proportional to a magnetization of the chip. A conclusion can thereby be drawn from the magnetization about the chip size and/or the chip material.

It is preferably proposed that the chip classifier evaluates an out-of-phase component for identifying a hardness of the chip and/or a chip material, said component further being further proportional to an area under a hysteresis curve of the chip. The so-called out-of-phase component is thereby also known from signal processing and is determined in that demodulation of the exciter signal and of the chip signal is performed at a fixed, phase-shifted reference frequency. The out-of-phase component is also known as the "quadrature." It has been realized here that the out-of-phase component is proportional to an area under a hysteresis curve of the chip. It has also been realized that the area under the hysteresis curve allows a conclusion about the hardness of the chip to be drawn. For example, a narrow hysteresis curve having a large saturation magnetization is an indicator of a low hardness (magnetically soft) and a wide and shallower hysteresis curve, in comparison, is an indicator of a higher hardness (magnetically hard). Thus, for example, different hardness classes can be determined by evaluating the out-of-phase component.

It is understood that the in-phase component and the out-of-phase component are determined from the exciter signal and/or the chip signal, for example by means of a frequency analysis.

It is thus proposed to perform an I&Q method (in-phase & quadrature method) in order to obtain phase information by means of said demodulation.

It is preferably also proposed that the exciter signal is an alternating voltage signal, for example a sinusoidal, a triangular, or a rectangular alternating voltage signal. The use of an alternating voltage signal as the exciter signal is advantageous because the chip signal can be measured multiple times and at a phase sift, because said signal is repeatedly excited by the alternating voltage signal. The alternating voltage signal may also be implemented as an alternating current signal.

In one further embodiment, it is proposed that the exciter signal has a frequency in a frequency range from 100 Hz to 10 kHz. Said frequency range is a frequency range by means of which the penetration depth of the exciter signal can also be adjusted, and thus the chip signal can be tuned, for example whenever said signal is not sufficiently measurable.

It is preferably proposed that the frequency of the exciter signal is varied in a predefined sequence in order to vary a penetration depth of the exciter signal into the chip. It is thus proposed that the exciter signal is not operated at a constant frequency, but rather a frequency change is performed. In a concrete example, a first frequency is first set for a first period of time, then the frequency is changed and a second frequency is set for a second period of time. Thus the penetration depth of the exciter signal into the chip as a magnetic signal can also be adjusted.

In a preferred embodiment, the signal generator is configured to generate the electrical exciter signal having a sinusoidal curve, and/or a triangular curve, and/or a rectangular curve, in order to set a penetration depth of the exciter signal into the chip. The electrical exciter signal is particularly preferably implemented having a sinusoidal curve, because the sinusoidal signal induces fewer harmonics in the chip signal.

It is preferably proposed that the chip classifier comprises a material database, wherein material data is stored in the material database.

In a particularly preferred embodiment, material data is provided here as comparative data, such as coercive field strengths, susceptibilities, remanences, magnetic saturations, or hysteresis curves. The material data is thereby implemented to be able to be interpolated and can be stored as data sets in a memory unit. The memory for the material data may be part of the chip classifier or may be an external database. It is understood that, in the latter case, the chip classifier is accordingly configured to read out from the external database.

It is further preferably proposed that the chip classifier is configured to determine at least one first hardness class and/or one second hardness class of the chip by comparing with the material data. The first hardness class may be a hardness class indicating that the classified chip is magnetically soft. The second hardness class may be a hardness class indicating that the classified chip is magnetically hard. Further intermediate gradations of hardness classes may also be provided.

In addition or alternatively, it is further proposed that the chip classifier is configured to determine at least one chip size of the chip by comparing with the material data. The chip size may also be construed as the volume, as described above. For example, the chip size can be determined from the comparative data described above.

In addition or alternatively, it is preferably proposed that the chip classifier is configured to determine at least one chip material of the chip by comparing with the material data. The chip material describes the material of which the chip is made, such as hardened steel.

The material data preferably comprises at least one comparative signal curve. It is thus proposed that at least one comparative signal curve is part of the material data and the captured chip signal can be compared with the comparative signal curve. A plurality of comparative signal curves may also be stored in the material data and may be construed as a characteristic map. It is accordingly proposed to classify the chip to be classified in the chip analysis area by comparing with the at least one comparative signal curve, for example in order to determine the hardness of the chip, the chip size, or the chip material.

In a particularly preferred embodiment, it is proposed that the presence of the first and/or second hardness class is determined by comparing the chip signal with the comparative signal curves. The chip classifier is preferably configured to determine a presence of the first and/or second hardness class by comparing the chip signal with the comparative signal curves.

In a preferred embodiment, it is proposed that the chip classifier is implemented having a plurality of receiving coils, wherein the receiving coils are disposed distributed over a sensor surface within a sensor head. In addition or alternatively, it is proposed that the chip classifier is implemented having a plurality of Hall-effect sensors and/or magnetoresistive sensors, wherein the Hall-effect sensors and/or magnetoresistive sensors are disposed distributed over a sensor surface within a sensor head. By using a plurality of receiving coils, a location of the chip can be determined and provided. By using a plurality of Hall-effect sensors and/or magnetoresistive sensors, a location of the chip can also be determined and provided. The location determination thereby relates to the location of the chip on the sensor head. The location determination is provided for detecting a plurality of different chips in order to provide an independent characterization of different chips disposed on the sensor head.

By using a plurality of receiving coils, a size of the chip can be determined and provided in addition or alternatively. In addition or alternatively, by using a plurality of Hall-effect sensors and/or magnetoresistive sensors, a size of the chip can also be determined and provided in addition or alternatively. For example, when a chip is disposed across a plurality of receiving coils, the chip size can be determined by evaluating the chip signals of the receiving coils disposed near the chip to be classified. The reflected chip signal is most strongly present there.

The coils can be interconnected as an array to this end and can be read out individually by means of a selection circuit, for example by means of a multiplexer.

For example, when a chip is disposed across a plurality of Hall-effect sensors and/or magnetoresistive sensors, the chip size can be determined by evaluating the chip signals of the Hall-effect sensors and/or magnetoresistive sensors disposed near the chip to be classified. The reflected chip signal is most strongly present there.

The Hall-effect sensors and/or magnetoresistive sensors can be interconnected as an array to this end and can be read out individually by means of a selection circuit, for example by means of a multiplexer or bus system.

The receiving coils are preferably disposed distributed in a honeycomb pattern within a sensor head. In addition or alternatively, the Hall-effect sensors and/or magnetoresistive sensors are disposed distributed in a chessboard pattern within a sensor head, that is, rectangularly adjacent to each other in two directions, like a chessboard. The packing density can thus be increased.

The at least one receiving coil preferably comprises a coil axis implemented substantially at a normal orientation relative to a sensor surface plane. Said orientation to the sensor surface thereby makes it possible to minimize the influence of the exciter signal on the chip signal. By means of said arrangement, an excitation field oriented normal to the receiving coil is generated. The influence of the exciter signal on the receiving coil is thus minimized. In addition or alternatively, the at least one Hall-effect sensor and/or magnetoresistive sensor comprises at least one sensor axis implemented at a normal orientation relative to a sensor surface plane, particularly in order to minimize the influence of the exciter signal on the chip signal. It is thus proposed that the Hall-effect sensor and/or magnetoresistive sensor is oriented so as to measure the exciter signal as little as possible or at least such that at least one axis of a multi-axis sensor measures the exciter signal as little as possible. In a preferred embodiment, the at least one Hall-effect sensor and/or the at least one magnetoresistive sensor is implemented having multiple axes, particularly three axes. The influence of the exciter signal on the receiving coil is thus minimized.

The sensor device preferably comprises a chip collector in order to hold the at least one chip to be classified in the chip analysis area. It is thus proposed that a device is provided for holding the chip or chips to be classified stationary in the chip analysis area. This may also be construed as capturing the chip or chips.

In a preferred embodiment, it is proposed that the chip collector is configured to magnetically hold the at least one chip to be classified by means of a magnetic field in the chip analysis area. To this end, the chip collector may be implemented as a coil, for example, supplied with a direct current. The chip collector may also be implemented having a magnet, for example a permanent magnet.

In addition or alternatively, it is proposed in a preferred embodiment that the chip collector is configured to magnetically hold the at least one chip to be classified by means of a magnetic field in the chip analysis area. To this end, the chip collector may be implemented having a metal mesh or having a basket or net.

It is preferably proposed that the chip collector is configured as a coil driven by a direct current to magnetically hold the at least one chip to be classified by means of a magnetic field in the chip analysis area. An adjustable magnetic field can be implemented advantageously by means of a coil driven by direct current. The magnetic collector can thus be switched off as needed.

In a further preferred embodiment, the magnetic field is implemented to be switched on and off by means of a control unit. A cleaning of the chip area can thus be implemented, for example. For maintenance, the magnetic field of the chip collector can be switched off. After switching off, the chips are no longer magnetically held by the chip collector and can thus be easily removed.

The chip analysis area is preferably a spatial region within a line through which a liquid flows. It is thus proposed that the sensor device can be installed and used in all lines through which a liquid flows, such as a line of a lubrication circuit or a cooling circuit.

The previously described sensor device can accordingly also be introduced into any arbitrary line through which a liquid flows.

In a preferred embodiment, the liquid is oil and/or a liquid coolant, and the line is further preferably a lubrication and/or a coolant line.

It is preferably proposed that the chip classifier is set up for providing the chip signal to an external processing unit by means of a communication unit for external evaluation.

It is preferably proposed that the chip classifier is configured to provide a result of the evaluation by means of a communication unit, wherein the result of the evaluation is particularly a classified hardness class, a classified chip size, and/or a classified chip material. The result of the evaluation or the classification can thus be processed further and provided to a process computer for process monitoring, for example, or analyzed by means of an analysis unit, or provided to a reporting unit in order to indicate a need for maintenance or repair.

The signal generator is preferably configured to provide the exciter signal as a reference signal to the chip classifier and/or to an external processing unit by means of a communication unit.

The external processing unit is an external process computer or an external control unit, for example. The external process computer or the external control unit may be part of the technical system in which the sensor device is used.

It is preferably proposed that the chip classifier comprises a computing unit in order to classify the at least one chip in the chip analysis area by evaluating a phase shift between the exciter signal and the chip signal and/or an amplitude of the chip signal; and/or in order to classify the at least one chip in the chip analysis area as a function of the chip signal and/or the exciter signal by means of an evaluation method.

The computing unit may be an internal computing unit as part of the sensor device, such as a microcontroller. The computing unit may also be an external computing unit, such as an external process computer or an external control unit.

According to the invention, a method for characterizing a chip by means of a sensor device comprising at least one signal generator and one chip classifier is also proposed.

The method comprises the steps: generating an electrical exciter signal by means of the signal generator having a transmitting coil, wherein the signal generator is configured to generate an electrical exciter signal and to couple said signal into a chip analysis area by means of the transmitting coil, wherein the chip analysis area is a spatial region;

receiving a chip signal by means of the chip classifier
      having at least one receiving sensor, wherein the chip
      classifier is configured to receive the chip signal from
      the chip analysis area by means of the receiving sensor,
      wherein the chip signal is a magnetization signal
      excited by the exciter signal and generated by at least
      one chip to be classified;
   evaluating the chip signal by means of the chip classifier,
      wherein the chip classifier is configured to classify the
      at least one chip in the chip analysis area by evaluating
      a phase shift between the exciter signal and the chip
      signal and/or an amplitude of the chip signal.

In a particularly preferred embodiment, the sensor device is implemented according to any one of the preceding embodiments.

The evaluating step preferably further comprises the steps:

determining a chip size and/or a chip material of the chip
      to be classified by determining an in-phase component
      by means of the chip classifier, preferably proportional
      to a magnetization of the chip, and/or
   determining at least one hardness class and/or one chip
      material of the chip to be classified by determining an
      out-of-phase component preferably proportional to an
      area under a hysteresis curve of the chip.

The explanations, advantages, and embodiments of the sensor device described above for characterizing a chip applying analogously to the present method for characterizing a chip by means of a sensor device.

The invention is described in more detail below, using embodiment examples and referencing the accompanying figures, wherein the same reference numerals are used for identical or similar components:

FIG. 1 schematically shows a lubrication circuit of a transmission having a sensor device in one embodiment.

FIG. 2 schematically shows a block diagram of a sensor device according to the invention in one embodiment.

FIG. 3 schematically shows a part of a sensor device in one embodiment introduced into a line through which a liquid flows.

FIG. 4 schematically shows a side section view of a part of a sensor device having a primary coil and a plurality of receiving coils in one embodiment.

FIG. 5 schematically shows a top section view of a part of a sensor device having a plurality of receiving coils in one embodiment.

Figure 8:
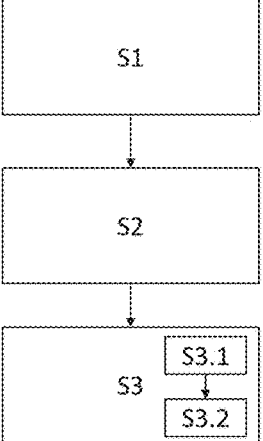

FIG. 8 schematically shows a flow chart of the method according to the invention in one embodiment.

Figure 1:
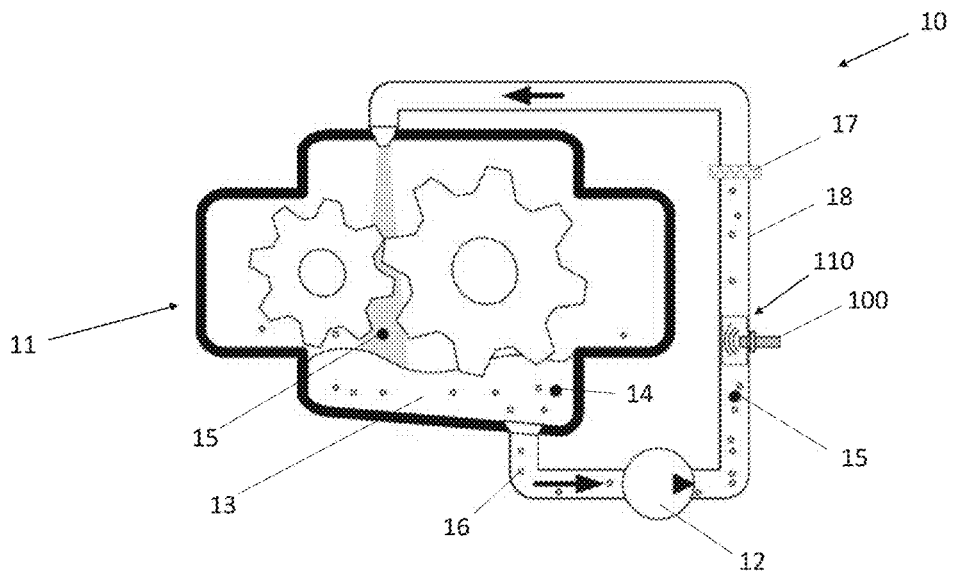

FIG. 1 shows a lubrication circuit 10 of a transmission 11 having a sensor device 100 in one embodiment. The transmission 11 is shown as a spur gear transmission for illustration purposes.

A pump 12 is part of the lubrication circuit 10 and is configured to pump lubricating oil 13 in the circuit. The lubricating oil 13 is provided for reducing wear of the transmission 11 and reduces the mechanical friction in the spur gear transmission shown. Due to the mechanical loads on the transmission, wear indications such as surface pitting or ablations from transmission components can arise. The wear or the detached transmission material thus enters the lubrication circuit 10 and is present in the lubrication circuit as artifacts in the form of metal particles or metal chips 14,15. For example, in FIG. 1, two magnetically hard chips or particles 15 and one magnetically soft chip or particle 14 are shown, potentially having detached at different points in time. In addition, other suspended matter 16 is also present in the lubrication circuit, such as non-metal dirt particles.

A filter 17 is provided for filtering out suspended matter 16 from the lubricating oil 13. The metal chips are filtered by the sensor device 100. The sensor device preferably comprises a chip collector in order to hold the at least one chip to be classified or the chips 14, 15 to be classified in the chip analysis area 110.

The sensor device 100 for characterizing the chip is part of the lubrication circuit 10. The sensor device 100 is implemented as shown in FIG. 2, 3, 4, or 5, for example. The sensor device 100 is introduced into the line 18 through which liquid flow and comprises a chip analysis area 110 as a spatial region within the line 18, shown as a dotted area.

The sensor device 100 comprises a signal generator, not shown in FIG. 1, having at least one transmitting coil, wherein the signal generator is configured to generate an electrical exciter signal and to couple said signal into the chip analysis area 110 as a magnetic signal by means of the transmitting coil. The coupling of the exciter signal as a magnetic signal into the chip analysis area 110 is depicted by field lines indicated in FIG. 1.

FIG. 1 shows a lubrication circuit 10 of a spur gear transmission. The sensor device 100 shown may also, however, be introduced into any other line 18 in which liquid flows.

The functional principle of the sensor device 100 is not limited to a lubrication circuit 10 of a transmission, but rather may also be introduced in a coolant circuit or directly in a transmission, for example.

Figure 2:
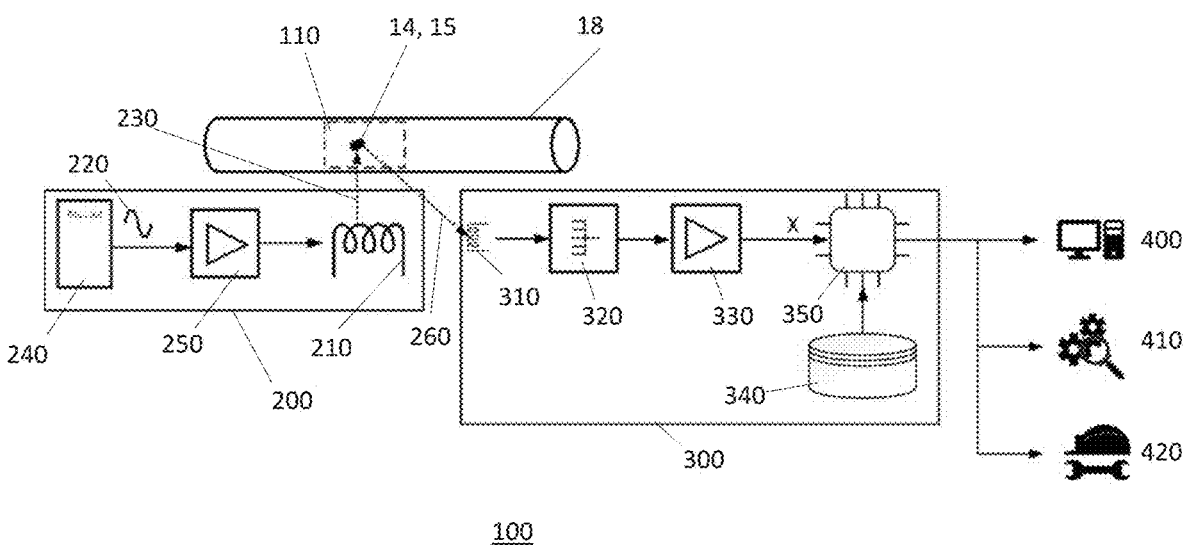

FIG. 2 schematically shows a block circuit diagram of a sensor device 100, such as is shown in FIG. 1, for example.

The sensor device 100 is provided for characterizing a chip 14, 15 and comprises a chip analysis area 110, wherein the chip analysis area 110 is a spatial region, for example within the line 18 through which liquid flows, as shown in FIG. 1.

The sensor device 100 comprises a signal generator 200 having at least one transmitting coil 210, wherein the signal generator is configured to generate an electrical exciter signal 220 and to couple said signal into a chip analysis area 110 as a magnetic signal 230 by means of the transmitting coil 210. The electrical exciter signal 220 may be generated, for example, by means of a function generator 240 as a sinusoidal alternating voltage signal at a frequency in a frequency range from 100 Hz to 10 kHz. The frequency of the exciter signal 220 can be varied in this case in a predefined sequence in order to adjust the penetration depth into the chip 14, 15.

An amplifier 250 may also be provided in order to amplify the electrical exciter signal 220.

The electrical exciter signal 220 is transformed into a magnetic signal 230 in the transmitting coil and thus couples into the chip analysis area 110. The magnetic signal 230 excites the chip 14, 15 magnetically, so that a characteristic and measurable chip signal 260 is generated on the basis of the excitation by the magnetic signal 230.

The sensor device further comprises a chip classifier 300 having at least one receiving sensor 310, wherein the chip classifier 300 is configured to receive a chip signal 260 from the chip analysis area 110 by means of the receiving coil. The receiving coil may thus also be construed as a measurement coil. The chip signal 260 is a magnetization signal excited by the exciter signal and generated by at least one chip 14, 15 to be classified.

In addition or alternatively to the receiving coil, at least one Hall-effect sensor and/or one magnetoresistive sensor may be used. A use of the receiving coil is shown in the embodiment examples.

The chip classifier 300 is configured to classify the at least one chip 14, 15 in the chip analysis area 110 by evaluating a phase shift between the exciter signal 220 and the chip signal 260 and/or an amplitude of the chip signal 260.

For example, the chip classifier 300 evaluates an in-phase component for identifying a chip size of the chip 14, 15 and/or a chip material of the chip 14, 15, said component being proportional to a magnetization of the chip. In addition or alternatively, the chip classifier 300 evaluates an out-of-phase component for identifying a hardness of the chip 14, 15 and/or a chip material of the chip 14, 15, said component being proportional to an area under a hysteresis curve of the chip, as is shown as an example in FIGS. 6 and 7.

The chip classifier 300 may also comprise an amplifier 330 in order to amplify the chip signal 260 measured by means of the receiving coil 310 in a desired working range.

Figure 4:
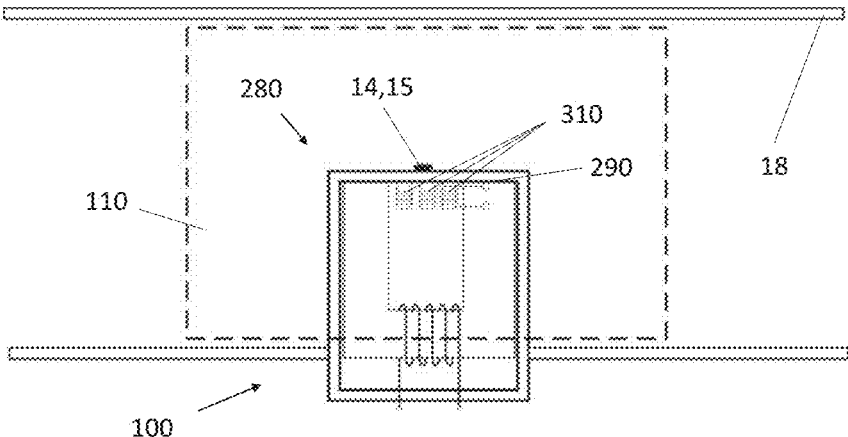
Figure 5:
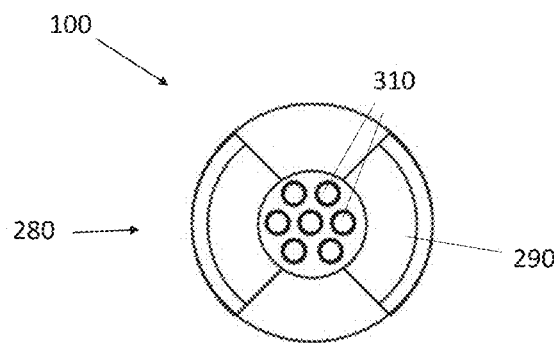

If the chip classifier 300 is implemented having a plurality of receiving coils 310, wherein the receiving coils 310 are disposed distributed over a sensor surface within a sensor head in order to provide a determination of the location of the chip, such as is shown in FIGS. 4 and 5, then a selection circuit 320, such as a multiplexer, may also be provided in order to evaluate the plurality of receiving coils 310 independently of each other.

The chip classifier 300 may also comprise a material database 340, wherein material data is stored in the material database, such as coercive field strengths, susceptibilities, remanences, magnetic saturations, or hysteresis curves.

The chip classifier 300 is configured to determine with a computing unit 350 at least one first hardness class and/or one second hardness class, a chip size, and/or a chip material of the chip 14, 15 by comparing with the material data. Thus it can be determined, for example, whether a magnetically soft chip 14 or a magnetically hard chip 15 is present.

The chip size or the chip volume can also be determined and the material of the chip 14 or 15 can also be determined. A conclusion about critical or uncritical wear or critical or uncritical transmission damage can thus be drawn.

The computing unit 350 is implemented as a microcontroller, for example.

The material database 340 is depicted in FIG. 2 as part of the chip classifier, but may also be an external database, and the computing unit 350 may communicate with the external database by means of a communications module, for example.

The material data may also comprise comparative signal curves, wherein a presence of the first and/or second hardness class is determined by comparing the chip signal 260 with the comparative signal curves, namely by the computing unit. Thus a comparison takes place with a plurality of signal curves of the chip signal 260 stored in the material database 340. For example, the signal curves may be stored as a characteristic map in the material database 340.

After the chip classifier 300 has classified the at least one chip 14, 15 in the chip analysis area by evaluating a phase shift between the exciter signal 220 and the chip signal 260 and/or an amplitude of the chip signal 260, the result of the classification can be processed further and, for example, provided to a process computer 400 for process monitoring, or analyzed by means of an analysis unit 410, or provided to a reporting unit 420 in order to indicate a need for maintenance or repair.

Figure 3:
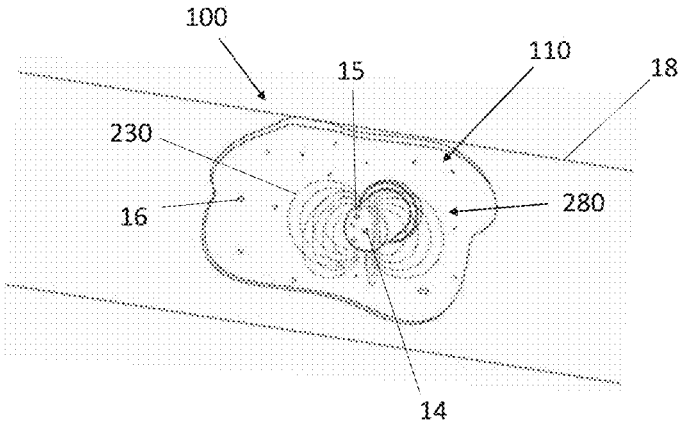

FIG. 3 shows a part of a sensor device 100 for characterizing a chip, such as is shown in FIG. 1 or 2. The sensor device 100 comprises a chip analysis area 110, preferably a spatial region within a line 18 through which a liquid flows. The sensor device 100 comprises a signal generator having at least one transmitting coil, not shown. The signal generator is configured to generate an electrical exciter signal 220 and to couple said signal into a chip analysis area 110 as a magnetic signal 230 by means of the transmitting coil, also not shown.

The sensor device 100 further comprises a chip collector 270 in order to hold the at least one chip 14, 15 to be classified in the chip analysis area 110, namely in a stationary manner at a sensor head of the sensor device 100. The chip collector 270 is shown only indirectly in FIG. 3, as a plurality of metal chips 14, 15 adhere to the sensor head of the sensor device 100. The chip collector 270 is configured to magnetically hold the at least one chip to be classified by means of a magnetic field in the chip analysis area 110. To this end, the chip collector may be configured as a coil driven by a direct current to magnetically hold the at least one chip 14, 15 to be classified by means of a magnetic field in the chip analysis area 110, wherein the magnetic field is implemented for switching on and off by means of a control unit for cleaning the chip area.

FIG. 4 shows a side section view of a part of a sensor device 100 having a transmitting coil 210 and a plurality of receiving coils 310. The receiving coils are disposed distributed over a sensor surface 290 within a sensor head 280 in order to provide a determination of the location and/or a determination of the size of the chip 14, 15.

The receiving coil 310 comprises a coil axis implemented at a normal orientation relative to the sensor surface plane 290 in order to minimize an influence of the exciter signal on the chip signal. The transmitting coil 210 in the embodiment shown further comprises a coil axis implemented substantially parallel relative to the sensor surface plane 290. The coil axis of the transmitting coil may alternatively be implemented substantially perpendicular relative to the sensor surface plane 290, particularly if the transmitting coil is wound about a perpendicular arm. By means of said alignment, the influence of the exciter signal coupled into the chip analysis area 110 as a magnetic signal 230 can be reduced and the chip signal can be measured in an improved manner, because the exciter field is normal to the receiving coil.

FIG. 5 depicts a part of a sensor device 100 having a plurality of receiving coils 310, wherein the receiving coils 310 are disposed distributed over a sensor surface 290 within a sensor head 280 in order to provide a determination of the location and/or a determination of the size of the chip 14, 15, wherein the receiving coils 310 are disposed distributed in a honeycomb pattern within a sensor head 280. The FIG. 5 shown is a top section view of FIG. 4, for example.

Figure 6:
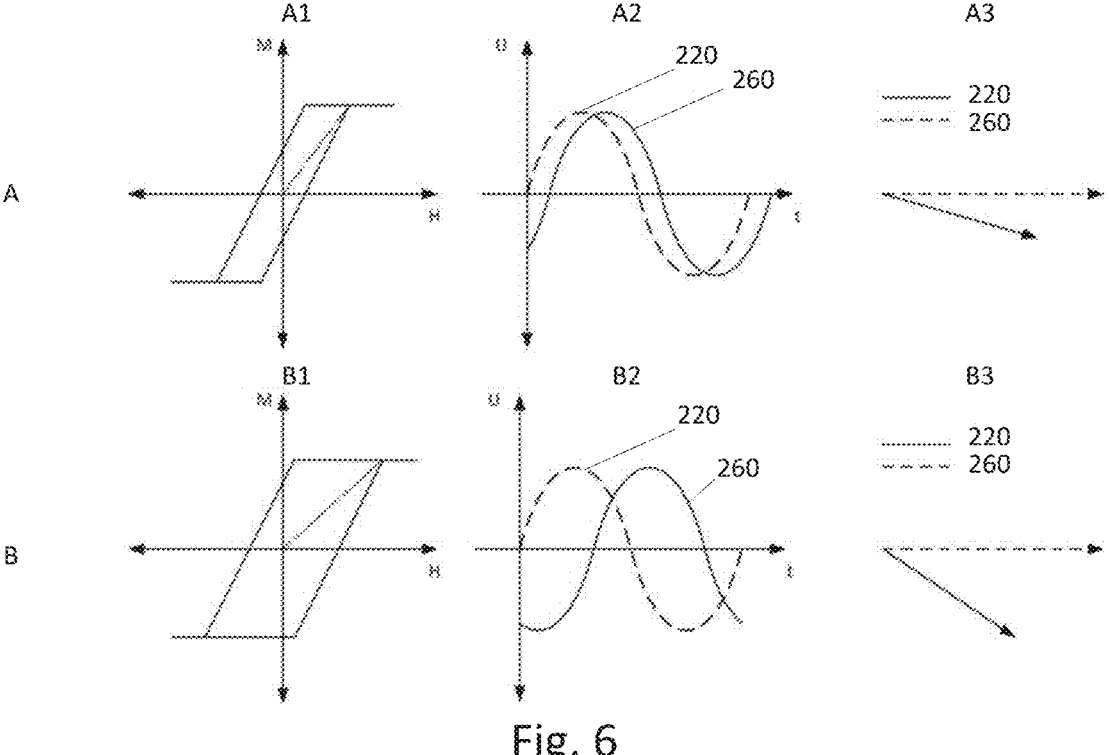
FIG. 6 shows six diagrams depicting an evaluation of a phase shift between the exciter signal and a chip signal and an evaluation of an amplitude of the chip signal.

FIG. 6 illustrates the evaluation principle for characterizing a chip. As described above, the chip classifier is configured to classify the at least one chip in the chip analysis area by evaluating a phase shift between the exciter signal and the chip signal and/or an amplitude of the chip signal. The chip classifier is thus configured to determine, for example, a chip size, a chip material, and/or a hardness class of the chip.

In the top area A are shown three diagrams A1 through A3 illustrating a characterization of a magnetically soft chip.

In the bottom area B are shown three diagrams B1 through B3 illustrating a characterization of a magnetically hard chip.

Two different hysteresis curves are shown in the diagrams A1 and B1. In both diagrams A1 and B1, the magnetization M is plotted on the Y-axis and the magnetic field strength H is plotted on the X-axis. The intersections of the curves with the Y-axis correspond to the positive and negative remanence. The intersections with the X-axis correspond to the positive and negative coercive field strength. The dotted lines correspond to the course of an initial magnetization curve. As can be seen, the curves A1 and B1 saturate in both the positive and negative directions, independently of whether the magnetic field strength is positively or negatively further increased. This is known as magnetic saturation. The two hysteresis curves thus also comprise a positive and negative magnetic saturation. As can be seen in diagram A1, a narrow hysteresis curve arises in comparison with diagram B1, leading to the conclusion of a soft chip. The hysteresis curve in diagram B1 is wider and lower in comparison with the diagram A1, so that a conclusion can be drawn of a magnetically hard chip. This relationship is illustrated in FIG. 6 and also in FIG. 7.

For example, the electrical exciter signal 220 and the chip signal 260 are illustrated in the diagrams A2 and B2. The voltage U is plotted over time t in the two diagrams A2 and B2. The voltage curves 220 and 260 are indeed illustrated in the same diagram, but the amplitude values of the signal curves 220 and 260 may be different.

As can be seen in Figures A2 and B2, a different phase shift arises between the electrical exciter signal 220 and the chip signal 260 due to the different material properties of the chips. For example, a chip signal generated by a magnetically soft chip is shown in diagram A2. Diagram B2 illustrates, as an example, a chip signal generated by a magnetically hard chip. By evaluating the phase shift, the chip can thus be classified, for example with respect to a hardness.

In addition or alternatively to the phase shift, it is also provided to evaluate the amplitude of the chip signal 260. The amplitude of the chip signal may be used as additional information to the phase shift because different chips implement different amplitudes in the chip signal curve when magnetically excited as a function of the electrical exciter signal.

Figures A3 and B3 fundamentally show the diagrams A2 and B2 in a different depiction, namely as a rotating space phasor. As can be seen, the space phasors 220 and 260 rotate synchronously with each other at a phase angle of various magnitude. Thus a phase shift can also be determined on the basis of the phase angle.

Figure 7:
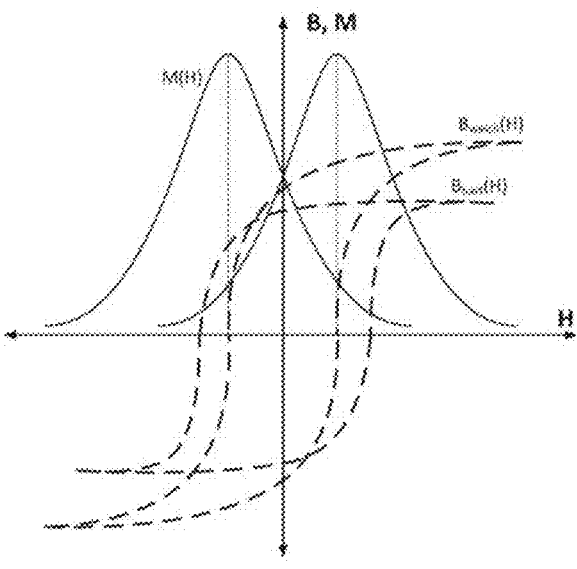
FIG. 7 shows a diagram in which two hysteresis curves are shown schematically.

FIG. 7 shows an example of two hysteresis curves plotted in a three-axis diagram. The magnetic field strength H is plotted on the X-axis. The magnetic flux density B is plotted on a first Y-axis and the magnetization M is plotted on a second Y-axis.

As can be seen, the magnetically hard and magnetically soft chips differ by different areas of the hysteresis curves. This realization is used to not only detect, but also to characterize, a chip in the chip analysis area, for example with respect to the size (chip volume), the magnetic properties (hardness), or the material properties (chip material) thereof.

FIG. 8 shows a flow chart of a method for characterizing a chip by means of a sensor device.

In a first step S1, generating an electrical exciter signal by means of a signal generator having a transmitting coil takes place, wherein the signal generator is configured to generate an electrical exciter signal and to couple said signal into a chip analysis area by means of the transmitting coil, wherein the chip analysis area is a spatial region.

In a second step S2, a receiving of a chip signal by means of a chip classifier having at least one receiving coil takes place, wherein the chip classifier is configured to receive the chip signal from a chip analysis area by means of the receiving coil, wherein the chip signal is a magnetization signal excited by the exciter signal and generated by at least one chip to be classified.

In a third step S3, evaluating the chip signal by means of the chip classifier takes place, wherein the chip classifier is configured to classify the at least one chip in the chip analysis area by evaluating a phase shift between the exciter signal and the chip signal and/or an amplitude of the chip signal.

In addition, two further preferred steps S3.1 and S3.2 are illustrated in step S3.

In step S3.1, determining a chip size and/or a chip material of the chip to be classified takes place by determining an in-phase component by means of the chip classifier, proportional to a magnetization of the chip.

In step 3.2, determining at least one hardness class and/or one chip material of the chip to be classified takes place by determining an out-of-phase component proportional to an area under a hysteresis curve of the chip.

As a further consideration, a sensor device for characterizing a chip is proposed, comprising a chip analysis area, wherein the chip analysis area is a spatial region, a signal generator having at least one transmitting unit, wherein the signal generator is configured to generate an electrical exciter signal and to couple said signal into the chip analysis area by means of the transmitting unit; a chip classifier having at least one receiving sensor, wherein the chip classifier is configured to receive a chip signal from the chip analysis area by means of the receiving sensor, wherein the chip signal is a magnetization signal excited by the exciter signal and generated by at least one chip to be classified, characterized in that the chip classifier is further configured to classify the at least one chip in the chip analysis area by evaluating a phase shift between the exciter signal and the chip signal and/or an amplitude of the chip signal.

Alternatively to the transmitting coil, it is thus proposed to use a signal generator having at least one transmitting unit, wherein the signal generator is configured to generate an electrical exciter signal and to couple said signal into the chip analysis area as a magnetic signal by means of the transmitting unit. It is thus proposed to use any other arbitrary technical apparatus instead of a transmitting coil in order to generate the electrical exciter signal.

Using a signal generator having at least one transmitting coil, wherein the signal generator is configured to generate an electrical exciter signal and to couple said signal into the chip analysis area as a magnetic signal by means of the transmitting coil, is an optional feature. A sensor device configured only to receive the chip signal and evaluating the chip signal may also be provided.

As a further consideration, a sensor device for characterizing a chip is thus proposed, comprising: a chip classifier having at least one receiving sensor, wherein the chip classifier is configured to receive a chip signal by means of the receiving sensor, wherein the chip signal is a magnetization signal excited by the exciter signal and generated by at least one chip to be classified, wherein the chip classifier is configured to classify the at least one chip by evaluating a phase shift between the exciter signal and the chip signal and/or an amplitude of the chip signal.

The present sensor device having a generic transmitting unit or without a signal generator is preferably implemented according to any one of the preceding embodiments.

The method step of generating an electrical exciter signal by means of the signal generator having a transmitting coil, wherein the signal generator is configured to generate an electrical exciter signal and to couple said signal into a chip analysis area by means of the transmitting coil, wherein the chip analysis area is a spatial region, is an optional feature. A method configured only to receive and evaluate the chip signal may also be provided.

As a further consideration, a method for characterizing a chip by means of a sensor device comprising at least one chip classifier is thus proposed. The method comprises the steps: receiving a chip signal by means of the chip classifier having at least one receiving sensor, wherein the chip classifier is configured to receive a generated chip signal by means of the receiving sensor, wherein the chip signal is a magnetization signal excited by the exciter signal and generated by at least one chip to be classified; and evaluating the chip signal by means of the chip classifier, wherein the chip classifier is configured to classify the at least one chip by evaluating a phase shift between the exciter signal and the chip signal and/or an amplitude of the chip signal. A measurement method is thus proposed.

The feature of classifying the at least one chip by evaluating a phase shift between the exciter signal and the chip signal and/or an amplitude of the chip signal is thus also an optional feature. It is generically proposed to evaluate the received chip signal for classifying the chip. It is thus proposed to evaluate a chip signal as a magnetic signal generated by excitation and generated in the chip as a reaction to the excitation. Known methods for characterizing a chip, in contrast, use comparative coils in order to characterize the chip using a change in impedance between a measurement coil and a reference coil, as described in the introduction above.

LIST OF REFERENCE NUMERALS

10 Lubrication circuit
11 Transmission
12 Pump
13 Lubricating oil
14,15 (Metal) chip (magnetically soft, magnetically hard)
16 Suspended matter
17 Filter
18 Line in which liquid flows
100 Sensor device
110 Chip analysis area

200 Signal generator
210 Transmitting coil
220 Exciter signal
230 Magnetic signal
240 Function generator
250 Amplifier
260 Chip signal
270 Chip collector
280 Sensor head
290 Sensor surface plane
300 Chip classifier
310 Receiving coil
320 Selection circuit
330 Amplifier
340 Material database
350 Computing unit
400 Process computer
410 Analysis unit
420 Reporting unit

The invention claimed is:

1. A sensor device (100) for characterizing a chip (14,15), comprising:
   a chip analysis area (110), wherein the chip analysis area is a spatial region;
   a signal generator (200) having a transmitting coil (210), wherein the signal generator is configured to generate an electrical exciter signal (220) and to couple said signal as a magnetic signal (230) into the chip analysis area via the transmitting coil;
   a chip classifier (300) having a receiving sensor (310), wherein the chip classifier is configured to receive a chip signal (260) from the chip analysis area via the receiving sensor, wherein the chip signal is a magnetization signal excited by the exciter signal and generated by a chip (14,15) to be classified, wherein
   the chip classifier (300) is further configured to classify the chip (14,15) in the chip analysis area (110) by evaluating a phase shift between the exciter signal (220) and the chip signal (260) and/or an amplitude of the chip signal (260).

2. The sensor device (100) according to claim 1, wherein the receiving sensor comprises a receiving coil implemented for receiving the chip signal.

3. The sensor device (100) according to claim 1, wherein the receiving sensor is implemented having a receiving element configured to utilize a Hall effect and/or a magnetoresistive effect for receiving the chip signal.

4. The sensor device (100) according to claim 1, wherein the chip classifier (300) evaluates an in-phase component for identifying a chip size of the chip and/or a chip material of the chip, said component being proportional to a magnetization of the chip.

5. The sensor device (100) according to claim 1, wherein the chip classifier (300) evaluates an out-of-phase component for identifying a hardness of the chip and/or a chip material, said component being proportional to an area under a hysteresis curve of the chip.

6. The sensor device (100) according to claim 1, wherein the exciter signal (220) is an alternating voltage signal, particularly a sinusoidal, a triangular, or a rectangular alternating voltage signal.

7. The sensor device (100) according to claim 1, wherein the exciter signal (220) has a frequency in a frequency range from 100 Hz to 10 kHz.

8. The sensor device (100) according to claim 7, wherein the frequency of the exciter signal (220) is varied in a predefined sequence in order to vary a penetration depth of the exciter signal into the chip (14,15).

9. The sensor device (100) according to claim 1, wherein the signal generator (200) is configured to generate the electrical exciter signal (220) having a sinusoidal curve, and/or a triangular curve, and/or a rectangular curve, in order to set a penetration depth of the exciter signal into the chip.

10. The sensor device (100) according to claim 1, wherein the chip classifier (300) comprises a material database (340), wherein material data is stored in the material database, and
   (i) the chip classifier (300) is set up for determining a first hardness class and/or one second hardness class of the chip by comparing with the material data, and/or
   (ii) the chip classifier (300) is set up for determining a chip size of the chip by comparing with the material data, and/or
   (iii) the chip classifier (300) configured to determine a chip material of the chip by comparing with the material data.

11. The sensor device (100) according to claim 10, wherein the material data comprises a comparative signal curve, wherein a presence of the first and/or second hardness class is determined by comparing the chip signal with the comparative signal curve.

12. The sensor device (100) according to claim 1, wherein the chip classifier (300) comprises a plurality of receiving coils (310) and/or a plurality of Hall-effect sensors and/or a plurality of magnetoresistive sensors, and wherein the receiving coils and/or the Hall-effect sensors and/or the magnetoresistive sensors are disposed distributed over a sensor surface (290) within a sensor head (280), particularly in order to provide a determination of a location of the chip and/or a determination of a size of the chip, wherein the receiving coils and/or the Hall-effect sensors and/or the magnetoresistive sensors are disposed distributed in a honeycomb and/or chessboard pattern within a sensor head.

13. The sensor device (100) according to claim 12, wherein a receiving coil (310) selected from the plurality of receiving coils comprises a coil axis and/or the Hall-effect sensor comprises a sensor axis and/or the magnetoresistive sensor comprises a sensor axis implemented at a normal orientation relative to a sensor surface plane, particularly in order to minimize an influence of the exciter signal on the chip signal.

14. The sensor device (100) according to claim 1, further comprising a chip collector (270) in order to hold the chip (14,15) to be classified in the chip analysis area (110), the chip collector being configured to magnetically hold via a magnetic field the chip to be classified in the chip analysis area and/or to mechanically hold said chip via a fluid-permeable filter structure in the chip analysis area.

15. The sensor device (100) according to claim 14, wherein the chip collector (270) is configured as a coil driven by a direct current to magnetically hold via a magnetic field the chip to be classified in the chip analysis area, and the magnetic field is implemented for switching on and off via a control unit, particularly for cleaning the chip area.

16. The sensor device (100) according to claim 1, wherein the chip analysis area (110) is a spatial region within a line (18) through which a liquid flows, and the liquid is oil and/or a liquid coolant, and the line is further a lubrication and/or a coolant line.

17. A method for characterizing a chip (14,15) via a sensor device (100) comprising a signal generator (200) and one chip classifier (300), comprising the steps:

generating (S1) an electrical exciter signal (220) via the
signal generator (200) having a transmitting coil (210),
wherein the signal generator is configured to generate
the electrical exciter signal and to couple said signal
into a chip analysis area as a magnetic signal via the
transmitting coil, wherein the chip analysis area is a
spatial region;

receiving (S2) a chip signal (260) via the chip classifier
(300) having a receiving sensor (310), wherein the chip
classifier is configured to receive the chip signal from
the chip analysis area (110) via the receiving sensor,
wherein the chip signal is a magnetization signal
excited by the exciter signal (220) and generated by a
chip (14, 15) to be classified;

evaluating (S3) the chip signal (260) via the chip classifier
(300), wherein the chip classifier is configured to
classify the chip (14,15) in the chip analysis area (110)
by evaluating a phase shift between the exciter signal
(220) and the chip signal (260) and/or an amplitude of
the chip signal (260), wherein the sensor device is implemented according to claim 1.

18. The method according to claim 17, wherein the
evaluating further comprises:

determining a chip size and/or a chip material of the chip
(14,15) to be classified by determining an in-phase
component via the chip classifier proportional to a
magnetization of the chip.

19. A sensor device (100) for characterizing a chip (**14,
15**), comprising:

a chip classifier (300) having a receiving sensor (310),
wherein the chip classifier is configured to receive a
chip signal (260) via the receiving sensor, wherein the
chip signal is a magnetization signal excited by the
exciter signal and generated by a chip (14,15) to be
classified, wherein the chip classifier (300) is further configured to classify
the chip (14,15) by evaluating a phase shift between the
exciter signal (220) and the chip signal (260) and/or an
amplitude of the chip signal (260).

20. The method according to claim 18, wherein the
evaluating further comprises:

determining a hardness class and/or one chip material of
the chip (14, 15) to be classified by determining an
out-of-phase component proportional to an area under
a hysteresis curve of the chip.

* * * * *